United States Patent [19]

Carr et al.

[11] 4,261,698
[45] Apr. 14, 1981

[54] TRACE OXYGEN DETECTOR

[75] Inventors: Timothy W. Carr, Poughkeepsie; Charles D. Needham, Wappingers Falls; Edward C. Spaulding, Poughkeepsie, all of N.Y.

[73] Assignee: International Business Machines Corporation, Armonk, N.Y.

[21] Appl. No.: 114,549

[22] Filed: Jan. 23, 1980

[51] Int. Cl.³ .................... G01N 27/66; G01N 21/31
[52] U.S. Cl. .................... 23/232 E; 422/83; 422/88; 422/98
[58] Field of Search .................... 422/88, 50, 83, 98; 23/232 R, 232 E; 73/23, 23.1

[56] References Cited

U.S. PATENT DOCUMENTS

| 3,647,387 | 3/1972 | Benson et al. | 23/232 E |
| 3,752,652 | 8/1973 | Vleesschauwer | 23/232 R |
| 4,147,515 | 4/1979 | Hass et al. | 23/232 E |
| 4,169,708 | 10/1979 | Muggli | 23/232 E |

OTHER PUBLICATIONS

Carr, "Comparison of the Neg. React. Ions Formed in the Plasma Chroma. by $N_2$, Air, and Sulfur Hexafluoride as the Drift Gas with Air as the Carrier Gas", Anal. Chem., vol. 51, No. 6, May 1979, pp. 705-711.

Primary Examiner—R. E. Serwin
Attorney, Agent, or Firm—Henry Powers

[57] ABSTRACT

Apparatus and a method for measuring trace amounts of oxygen in an atmosphere is described. An oxygen free nitrogen gas is used as the carrier gas and nitrogen, ultra high purity, with approximately 10 ppm (parts per million) water is used as the reagent gas of an ionization source is operated at atmospheric pressure. A small electric field of approximately 200 volts per centimeter is applied across the length of the ionization chamber up to a pinhole entrance to a quadrupole mass spectrometer. The voltage is biased to repel negative ions towards the quadrupole mass spectrometer. Measurement of the peak height of the m/e value of 52 in the mass spectrum are integrated over a period of time. The results of the integration are then compared to a calibration chart which indicates the amount of oxygen that is present in the atmosphere being measured.

15 Claims, 3 Drawing Figures

TRACE OXYGEN DETECTOR

DESCRIPTION

1. Technical Field

This invention relates to means for measuring trace amounts of oxygen, and more particularly to apparatus and method for monitoring trace amounts of oxygen in semiconductor fabricating processes.

One object of the present invention is to provide a novel method and apparatus for measuring trace amounts of oxygen over a wide dynamic range extending from parts per billion (ppb) to percent amounts of oxygen.

Another object of the present invention is to provide means for monitoring trace amounts of oxygen in semiconductor device fabrication processes.

Another object of the present invention is to provide a method and apparatus for measuring trace levels of oxygen in semiconductor manufacturing processing environments or levels adsorped on device surfaces.

2. Background Art

In the process of manufacturing semiconductor device and gaseous plasma display panels the presence of trace levels of oxygen either in the process environment or on the device surface could cause product failure either as a process yield or product reliability problem. For example, during chip joining a "thin skin" of oxide on the joining surfaces could cause bondability problems. As another example, trace levels (10 ppb to 100 ppm $O_2$) in the gas display panel can cause a failure in the plasma discharge. These examples demonstrate the need for a sensitive trace oxygen analyzer which can operate in the dynamic range of 1 part per billion (ppb) up to the percent level. Commercially available trace oxygen detectors which are on the market today have a lower limit of 0.1 part per million.

BRIEF DESCRIPTION OF THE DRAWINGS

In the accompanying drawings forming a material part of this disclosure.

DISCLOSURE OF THE INVENTION

The trace oxygen detector system described in this application can detect oxygen at the part per billion (ppb) level, with the advantage that it can detect oxygen that is present in the gas phase as well as oxygen that is adsorbed on a surface. Also by extending the method of this invention, the bond strength of the adsorped oxygen to the surface can be determined. The basis of the technique of this invention, is the formation (from the trace oxygen and controlled water) of a preferred $O(H_2O)_2^-$ ion of m/e (mass to charge ratio) of 52 formed at atmospheric pressure which is measured and related through a calibration curve to the concentration of oxygen. The formation of the $O(H_2O)_2^-$ ion will be described below.

Figure 1:
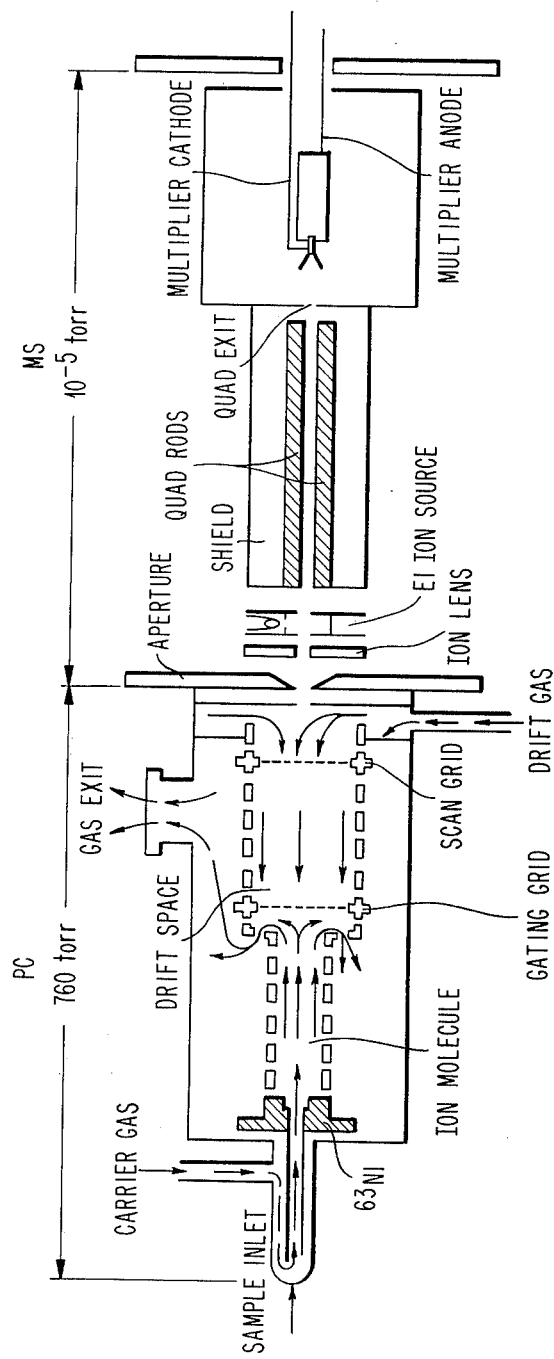
FIG. 1 is a schematic of a plasma chromatographmass spectrometer adapted for use in this invention.

Referring to FIG. 1 the instrument or apparatus comprises an atmospheric pressure ionization source, a reaction region, and a quadrupole mass spectrometer. The ionization source utilizes a $^{63}Ni$ foil for initiating the ionization process. Ultra high purity nitrogen $N_2$, is used as the carrier gas to bring the oxygen into the instrument. The method used to sample the trace oxygen and mix it with the carrier gas depends upon the state the oxygen exists in (gases or adsorped film). High purity nitrogen with 10 ppm water is used as the flush gas to flush out the ionization source and also supply the source of water for the clustering reaction with oxygen and as such can also be considered as the reagent gas. The ionization source is operated at atmospheric pressure with a small electric field of approximately 200 v/cm being applied across the ionization source and the length of the reaction region. The field is biased in such a way as to repel the negative ions down through the reaction region towards a pinhole aperature which separates the reaction region from the quadrupole mass filter section of the instrument. As the ions pass through the pinhole aperture (e.g. about 1 mil diameter) they are focused onto the quadrupole mass filter by an ion lens focusing arrangement. The quadrupole mass filter is tuned, in its context, to respond ony to m/e values of 32, 50, 52, and 68 which correspond to $O_2^-$, $O_2(H_2O)^-$, $O(H_2O)_2^-$ and $O_2(H_2O)_2^{31}$, respectively. An electron multiplier is mounted on the axis and serves as the detector for these ions. The specific mass filter section of this instrument operates at approximately $3\times10^{-5}$ TORR. A schematic diagram of this instrument is shown in FIG. 1.

The chemical reactions which take place in the ionization source at atmospheric pressure are very complex. The basic functional and preferred ion to be employed in this invention is the $O(H_2O)_2^{31}$ because it is very stable under analysis conditions. The $O_2^-$ molecular oxygen ion, which is the most familiar ion form of oxygen, is unstable and undergoes charge transfer reaction with other molecules. Therefore, the $O_2^-$ ion is undesirable in some applications. To keep the $O_2^-$ ion from forming in the ionization source, the temperature of the ionization source is maintained above 483° K. At 483° K. the coefficient of thermal detachment of an electron from the $O_2^-$ ion is greater than the coefficient of electron attachment.

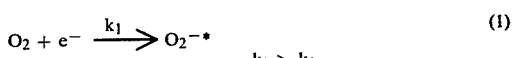

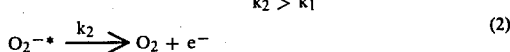

$$O_2 + e^- \xrightarrow{k_1} O_2^{-*} \quad (1)$$

$$k_2 > k_1$$

$$O_2^{-*} \xrightarrow{k_2} O_2 + e^- \quad (2)$$

As shown in reaction (1) when an electron is captured by oxygen it forms a highly energetically excited ion and at temperatures above 483° K. there is enough thermal energy to cause thermal electron detachment as shown in reaction (2). In other words, at temperatures above 483° K. the rate of reaction (2) is greater than the rate of reaction (1).

Therefore, at or above 483° K. the predominant mode of ionization for oxygen is by dissociative electron capture as shown in reaction (3).

$$O_2 + e^- \rightarrow O^- + O \quad (3)$$

$$O^- + 2H_2O \rightarrow O(H_2O)_2^- \quad (4)$$

The atomic oxygen ion will, under a hydration reaction in the presence of water, form the stable $O(H_2O)_2^-$ ion as shown in reaction (4). It is this ion which is monitored as a function of the oxygen concentration.

As the oxygen concentration of the gas to be measured increases into the percent range a side reaction starts to compete with reaction 2 as shown in reaction 5.

$$O_2^{-*} + O_2 \rightarrow O_2^- + O_2^*  \quad (5)$$

In reaction 5 molecular oxygen $O_2$, reacts with the excited molecular oxygen ion $O^{-*}$, and absorbs the excess energy and thus stabilizes the $O_2^-$ ion. A peak at m/e of 32 is noted in the mass spectrum. This ion can be used at higher (percent) concentration as a monitor of the oxygen concentration.

A significant advantage of this instrument or method is its wide dynamic range of operation; that is, parts per billion (ppb) to percent concentration of oxygen. Using this method/instrument it is possible to detect instantaneous changes in oxygen concentrations and therefore it can be used as a continuous oxygen monitor. The method/instrument is capable of being easily automated with any microprocessor or minicomputer such as an IBM Model 5100 or IBM Model 5110.

Another significant advantage is that no or very little sample preparation is needed (primarily because there is no vacuum associated with the sample housing).

BEST MODE FOR CARRYING OUT THE INVENTION

The Alpha-II plasma chromatograph/mass spectrometer manufactured by Franklin GNO Corporation was adapted for use in this invention. This instrument consists of a Beta-VII plasma chromatograph coupled to a specially modified Extranuclear Laboratories Spectr-Elquadrupole mass spectrometer. The operating parameters of the plasma chromatograph used in this study are summarized in Table I

TABLE I

| Operating Parameters of the Alpha-II Plasma Chromatograph-Mass Spectrometer | |
|---|---|
| Drift gas flow rate | 500 cc/min |
| Carrier gas flow rate | 100 cc/min |
| Applied voltage | ± 2800 V |
| Gate width | 0.2 msec |
| Repetition rate | 27.0 msec |
| Temperature | 210° C. |

A schematic of the combined PC-MS system is shown in FIG. 1. This instrument has the capability of operating in several modes so that ion mobility spectra, mass spectra, total ion mobility spectra, and mass identified mobility spectra can be obtained. The ionic mobility may be measured in either a one-grid or two-grid pulsing procedure with the Beta-VII plasma chromatograph mode of operation. Both grids of the drift tube are held open, allowing all the ions produced in the ionization source to continually drift down the tube and into the quadrupole mass spectrometer, which results in atmospheric pressure ionization mass spectra. Total ion mobility spectral can be obtained by operating the plasma chromatograph in the normal one-grid pulsing mode and the quadrupole mass spectrometer in the total ion mode, which enables the channeltron electron multiplier detector to measure the ionic distribution as a function of time. By adjusting the mass analyzer to respond only to a single m/e value and operating the plasma chromatograph in the normal one-grid pulsing mode, the distribution of an individual ion as a function of time can be obtained. The arrival time of the individual ions can then be compared with the arrival time of the ions measured in the total ion mode to produce the mass-identified mobility spectra.

A Nicolet Model SD-721A integrating ADC (analog-digital converter) mounted in a Nicolet Model 1074, 4096-channel signal averager was used to digitize the accumulated plasmagrams. Usually 512 scans of 27 ms duration were collected and stored on magnetic tape with a Nicolet Model NIC-28A magnetic tape coupler and Kennedy Model 9700 tape deck. As the data was being accumulated in memory, the information was displayed on a Tektronix Model D10 oscilloscope. The data stored on the magnetic tape was entered into an IBM System/370 computer and was subsequently analyzed using the VSAPL program under the operating system VM/370. The position and intensity of the peaks in the mobility spectra along with a plot of the mobility spectra were then displayed on a graphics terminal from which hard copies could be obtained.

The instrument consists of an atmospheric pressure ionization source, a reaction region, and a quadrupole mass instrument. The ionization source utilizes a $^{63}$Ni foil for initiating the ionization process. $^{63}$Ni emits a 60 keV B ray which is the source of electrons used for the formation of the $O(H_2O)_2^-$. Ultra high purity grade nitrogen, $N_2$, is used as the carrier gas to bring the oxygen containing gas into the instrument. The method used to sample the trace oxygen and mix it with the carrier gas depends upon the state in which the oxygen exist (namely a gas or absorbed on a surface). High purity nitrogen with 10 ppm water is used as the flush gas to flush out the ionization source and also to supply the source of water for the clustering reaction with the atomic oxygen ion and, as such, can also be considered as the reagent gas. The ionization source is operated at atmospheric pressure and at 210° C. (483° K.) or above. A small electric field of approximately 200 v/cm is applied across the ionization source and the length of the reaction region and is biased in such a way as to repel the negatively charged ions down through the reaction region towards a pinhole aperture which separates the reaction region from the guadrupole mass spectrometer section of the instrument. As the ions pass through the pinhole aperture they are focused into the quadrupole mass filter by an ion lens focusing arrangement. An electron multiplier is mounted on axis and serves as the detector for the ions. The mass spectometer section of this instrument operates at approximately $3 \times 10^{-5}$ mm Hg pressure.

Figure 2:
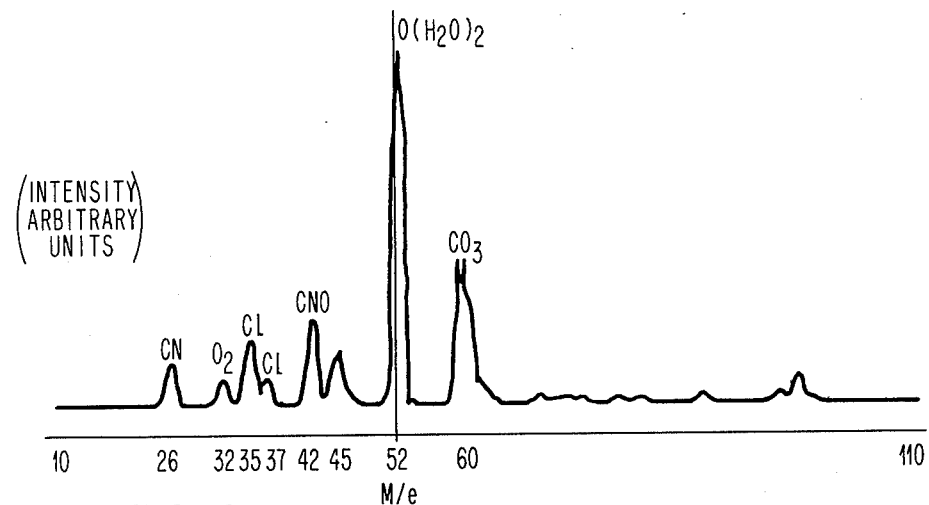
FIG. 2 is a graph illustrating the peaks in the negative ion mode spectrum of m/e (mass to charge ratio) of 52 and 32 recorded for a predetermined period of time.
Figure 3:
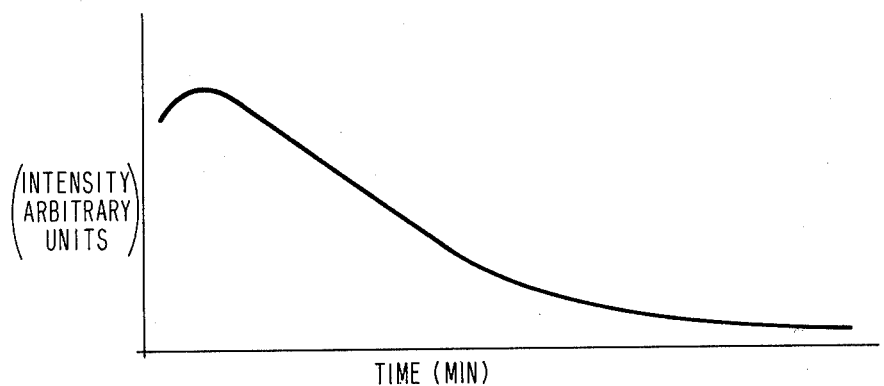
FIG. 3 illustrates the peak intensities of ions graphed as a function of time.

Oxygen concentration in a gas:

To determine the oxygen concentration of a gas, a known volume of the gas is mixed with the ultra high purity nitrogen carrier gas and allowed to enter the ionization source of the instrument. The peaks in the negative mode mass spectrum of m/e (mass to charge ratio) of 52 and 32 corresponding to the $O(H_2O)_2^-$ and $O_2^-$ ions are then recorded for a predetermined amount of time (FIG. 2 shows a typical negative mode mass spectrum). The peak intensities for the ions are then graphed as a function of time; as in FIG. 3. The area under this curve is then integrated and this value is compared to a calibration curve to determine the concentration of oxygen.

The calibration curve is derived from similar measurements made on gases containing known concentrations of oxygen. Spectra are obtained over a predetermined amount of time, intensities of the m/e = 52 peak are plotted as a function of time and the area under the curve is measured. The calibration curve consists of these area values graphed as a function of the known oxygen concentration.

Oxygen concentration as an absorbed layer on a surface:

To determine the amount of oxygen that is absorbed on a surface, the surface to be investigated must be placed in a container of known volume. The container must then be flushed out with nitrogen gas to remove the oxygen from the gas phase as a result of air. A flush of 30 min. to one hour is more than sufficient for this purpose. Next the container must be sealed off and heated to degas the absorbed oxygen from the surface. The oxygen is then measured as described above for the gaseous phase.

The system of this invention is characterized by the use of atmospheric pressure ionization using $^{63}$Ni; a negative ion made of operation; specific ion detection e.g. m/e 32 $[O_2^-]$, 50 $[O_2(H_2O)^-]$, the optimum and preferred 52 $[O(H_2O)_2^-]$, and 68 $[O_2(H_2O)_2^-]$; ultra high purity $N_2$ as a carrier gas; ultra high purity $N_2$ with 10 ppm $H_2O$ as a reagent gas; an ionization source temperature of at least 210° C.; and an electric field strength of 200 v/cm.

The instrument of this invention differs from conventional plasma chromatograph-mass spectrometers in that no gating or scan grids are employed and therefore there is no drift spectrometer and no ion mobility spectrum. The instrument of this invention also differs from an API (atmospheric pressure ionization) mass spectrometer in two ways: 1, a reagent gas is used in addition to a carrier gas and 2, the use of a reaction region with an applied electric field biased along it.

One unobvious feature is the use of the negatively charged oxygen water clusters to monitor the amount of oxygen. A particularly unobvious feature is the operation of the ionization source at or above 210° C. This feature is of prime importance to form the $O(H_2O)_2^-$ ion. This ion of m/e value of 52 is the preferred and optimum ion to be monitored at extremely low oxygen levels (sub picogram level), sub ppb). The ions of m/e 32, 50, and 68 can be used to monitor the oxygen level at high concentrations (ppm)

This instrument has the advantage that there is no vacuum associated with the sample inlet assembly and therefore there is very little sample preparation. Another significant advantage of this instrument is its wide dynamic range of operation e.g. ppb. to percent amount of oxygen.

This instrument will also respond to instantaneous changes in oxygen concentrations and therefore can be used as a continuous oxygen monitor. The instrument is capable of being easily automated with any microprocessor such as an IBM Model 5100.

While the invention has been illustrated and described with reference to preferred embodiments of this invention, it is to be understood that the invention is not to be limited to the precise constructions herein disclosed and the right is reserved to all changes and modifications coming within the scope of the invention as defined in the appended claims.

We claim:

1. Method for measuring trace amounts of oxygen comprising:
   (a) diluting said trace amounts of oxygen with inert gas carrier,
   (b) ionizing said oxygen to form ionized atomic oxygen,
   (c) reacting said ionized atomic oxygen with vapor to form ionized reaction products,
   (d) selectively separating said products into mass charge ratio values of 32, 50, 52, and 68, and,
   (e) measuring the quantities of said separated products in each of said values.

2. The method of claim 1 wherein said oxygen is ionized at a source temperature of at least 210° C. to form a $O(H_2O)_2^-$ ion of mass charge ratio 52.

3. The method of claim 2 wherein said measuring is specific to said mass charge ratio of 52.

4. The method of claim 2 wherein said oxygen is also ionized to form a $O_2^-$ ion of mass charge ratio of 32.

5. The method of claim 4 wherein said measuring includes said mass charge ratio of 32.

6. Apparatus for measuring low levels of oxygen comprising:
   (a) a chamber at atmospheric pressure and at a temperature of at least 210° C.,
   (b) means to introduce at one end an oxygen containing inert gas,
   (c) means to ionize the oxygen,
   (d) means to introduce a standard amount of water vapor into said chamber for reaction with the ionized oxygen to form ionized products,
   (e) means to bias the chamber to drive said products to the opposite end thereof,
   (f) a second chamber under vacuum at said opposite end,
   (g) an aperture in said opposite end interconnecting with said chambers to inject a stream of said products into said vacuum chamber, and
   (h) means at the end of said vacuum chamber to detect and measure the intensity of ions selected from the group of $O_2^-$, $O_2(H_2O)^-$, $O(H_2O)_2^-$ and $O_2(H_2O)_2^-$.

7. The apparatus of claim 6 wherein said means to ionize comprises $^{63}$Ni.

8. The apparatus of claim 6 wherein the first said chamber is biased with an electric field strength of 200 V/cm.

9. The apparatus of claim 8 wherein said means to ionize comprises $^{63}$Ni.

10. The apparatus of claim 6 including means to control said reaction to essentially the formation of the $O(H_2O)_2^-$ ion with a mass charge ratio of 52, and said filter is tuned to essentially a mass charge ratio of 52.

11. The apparatus of claim 10 wherein said means to ionize comprises $^{63}$Ni.

12. The apparatus of claim 11 wherein the first said chamber is biased with an electric field strength of 200 V/cm.

13. The apparatus of claim 6 including means to control said reaction to the formation of a stable $O_2^-$ ion having a mass charge ratio of 32, and said filter is tuned to said mass charge ratio of 32.

14. The apparatus of claim 13 wherein said means to ionize comprises $^{63}$Ni.

15. The apparatus of claim 11 wherein the first said chamber is biased with an electric field strength of 200 V/cm.

* * * * *